(12) United States Patent
Weber et al.

(10) Patent No.: US 7,601,382 B2
(45) Date of Patent: Oct. 13, 2009

(54) METHOD OF MAKING A COATED MEDICAL DEVICE

(75) Inventors: Jan Weber, Maple Grove, MN (US); Gordon Kocur, Lino Lakes, MN (US); Michael Helmus, Worcester, MA (US); Maria Palasis, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 779 days.

(21) Appl. No.: 10/914,012

(22) Filed: Aug. 5, 2004

(65) Prior Publication Data

US 2006/0030936 A1 Feb. 9, 2006

(51) Int. Cl.
*A61L 33/00* (2006.01)
*B05D 7/00* (2006.01)
*B05D 3/10* (2006.01)
*A61F 2/01* (2006.01)

(52) U.S. Cl. .............. 427/2.1; 427/2.24; 427/2.28; 427/212; 427/214; 427/331; 623/1.42

(58) Field of Classification Search .............. 427/212, 427/214, 331, 2.1–2.31; 623/1.42
See application file for complete search history.

(56) References Cited

U.S. PATENT DOCUMENTS

| 5,429,634 | A | | 7/1995 | Narisco, Jr. | |
|---|---|---|---|---|---|
| 5,824,049 | A | * | 10/1998 | Ragheb et al. | 623/1.44 |
| 6,071,305 | A | * | 6/2000 | Brown et al. | 623/1.43 |
| 6,394,094 | B1 | * | 5/2002 | McKenna et al. | 128/830 |
| 6,395,326 | B1 | * | 5/2002 | Castro et al. | 427/2.24 |
| 6,725,901 | B1 | | 4/2004 | Kramer et al. | |
| 6,752,829 | B2 | | 6/2004 | Kocur et al. | |
| 6,989,071 | B2 | | 1/2006 | Kocur et al. | |
| 7,273,493 | B2 | | 9/2007 | Ledergerber | |
| 2003/0065382 | A1 | | 4/2003 | Fischell | |
| 2003/0216803 | A1 | | 11/2003 | Ledergerber | |
| 2004/0039438 | A1 | | 2/2004 | Alt | |
| 2004/0116999 | A1 | | 6/2004 | Ledergerber | |
| 2005/0060020 | A1 | * | 3/2005 | Jenson | 623/1.13 |
| 2005/0085898 | A1 | | 4/2005 | Boatman | |
| 2005/0171596 | A1 | | 8/2005 | Furst | |
| 2008/0015676 | A1 | | 1/2008 | Kantor | |
| 2008/0097568 | A1 | | 4/2008 | Savage et al. | |

FOREIGN PATENT DOCUMENTS

EP 1466634 A1 * 10/2004

* cited by examiner

*Primary Examiner*—Timothy H Meeks
*Assistant Examiner*—Cachet I Sellman
(74) *Attorney, Agent, or Firm*—Vidas, Arrett & Steinkraus (57) ABSTRACT

Medical devices, such as stents, having a surface, a coating layer comprising a polymer disposed on at least a portion of the surface, and a composition comprising a biologically active material injected into or under the coating layer at one or more locations in the coating layer to form at least one pocket containing a biologically active material are disclosed. The composition may be injected using a nanometer- or micrometer-sized needle. Methods for making such medical devices are also disclosed. Using this method, a precise amount of the biologically active material may be disposed accurately and efficiently on the medical device at predefined locations.

40 Claims, 2 Drawing Sheets

METHOD OF MAKING A COATED MEDICAL DEVICE

1 FIELD OF THE INVENTION

This invention relates generally to medical devices for delivering a biologically active material to a desired location within the body of a patient. More particularly, the invention is directed to a method of a making a coated medical device by disposing a coating layer on the surface of the medical device and injecting precise amounts of a biologically active material into or under the coating layer.

2 BACKGROUND OF THE INVENTION

It has been common to treat a variety of medical conditions by introducing an insertable or implantable medical device such as stents, catheters or vena cava filters having a coating for release of a biologically active material into a body lumen of a patient. For example, various types of drug-coated stents have been used for localized delivery of drugs to a body lumen. See, e.g., U.S. Pat. No. 6,099,562 to Ding et al. Such coatings are generally manufactured by pre-mixing the drug with a dissolved polymer and using a spraying method or a dip coating method to deliver the mixture to the surface of the medical device. To spray the drug mixture, the drug must be well dispersed through a polymer coating mixture.

Also, because the drug or biologically active material can only tolerate a certain range of temperatures, the temperature at which the coating is dried or cured is restricted by the presence of the drug or biologically active material in the coating. More specifically, if the drug or biologically active material has a maximum temperature tolerance of 50° C., the polymer coating containing such drug or material should not be dried or cured above this temperature. Therefore, an application of a coating formulation that contains both a drug or biologically active material and polymer to a medical device can limit the temperature at which the coating is dried or cured and increase the amount of drying time required.

When a drug whose dosage must be strictly controlled is contained in the coating of such medical device, the amount of coating present on the medical device must be accurately adjusted. Previously, the only way to adjust the amount of coating on a medical device was to control the process parameters used to apply the coating composition onto the surface of the medical device to form the coating, such as controlling the application or spraying time and the flow rate of the coating solution. An improved method to manufacture a coated medical device having a strictly controlled amount of drug is needed.

In the conventional methods for coating medical devices, such as spray-coating or dipping, an entire surface or all surfaces of the medical device are coated even though it may be desired that only part of the surface is coated, or only some of the surfaces are coated. For instance, in medical devices having a tubular portion, such as a vascular stent, the inner surface of the tubular portion does not need to be coated with a coating containing a biologically active material that is used to treat only the body lumen wall that contacts the outer surface of the stent. When the entire outer surface of a medical device contains a biologically active material, this biologically active material can be delivered to both tissues in need of treatment, such as lesions and healthy body tissue.

Also, with existing coated medical devices, generally, the coating is uniformly applied along the entire length of the device or surface of the device. For example, conventional coated stents are coated uniformly along the entire length of their surface. By having the device uniformly coated along its length, the concentration release profile of the biologically active material along the length of the coated surface may be in the shape of a bell-curve, wherein the concentration of the biologically active material released at the middle of the surface is greater than the concentration of the biologically active material released at the ends of the coated surface.

Accordingly, there is a need for coated medical devices where the biologically active material can be positioned in predefined or selected regions of the medical device. Accordingly, there is a need for a method of applying a drug to the surface of a medical device. Also, there is a need for a method of making a coated medical device having a precise amount of a drug at predefined regions on the device and having a coating with a desired release profile.

3 SUMMARY OF THE INVENTION

These and other objectives are accomplished by the present invention. The present invention provides a method of making a medical device having a surface, wherein at least a portion of the surface is covered with a coating layer. This method comprises disposing a coating formulation comprising a polymer on at least a portion of the surface to form the coating layer. This method further comprises injecting a composition comprising a biologically active material into or under the coating layer at one or more locations to form at least one pocket containing the biologically active material. Preferably, the drug composition is injected into the coating layer using a micrometer- or nanometer-sized needle.

The present invention also provides a method of making a coated stent having a surface, wherein at least a portion of the surface is covered with a coating layer. In this embodiment, the method comprises providing a stent having a surface and disposing a coating formulation comprising a polymer on at least a portion of the stent surface to form a coating layer. The coating layer is substantially free of any biologically active material. The method also includes injecting a composition comprising a biologically active material into or under the coating layer using a micrometer- or nanometer-sized needle. The composition is injected into or under the coating layer at a plurality of locations to form a plurality of pockets containing the biologically active material.

The present invention further provides for a method of making a medical device having a surface, wherein at least a portion of the surface is covered with a coating layer. This method comprises disposing a first coating formulation comprising a first polymer on at least a portion of the surface to form a first coating layer, wherein the first coating layer is substantially free of any biologically active material. The method also comprises injecting a first composition comprising a first biologically active material into or under the coating layer, wherein the first composition is substantially free of a polymer. The first composition is injected into or under the coating layer at a plurality of locations to form a plurality of pockets containing the first biologically active material. This method may further comprise forming an additional coating layer by disposing a second coating formulation that comprises a second polymer over the first coating layer.

The present invention provides for an efficient, safe, and accurate method of manufacturing a medical device by depositing a precise amount of a biologically active material into a coating layer on the surface of the medical device at predefined locations to obtain a desired release profile of the biologically active material. Depositing desired amounts of a biologically active material at pre-defined locations is cost-effective because only necessary amounts are applied and the patient is exposed to necessary dosages of the biologically active material. The present method allows for the biologically active material to be applied to the medical device as a final step in the manufacturing process such as after the stent has been crimped on a balloon catheter. Thus, this method minimizes the risk of loss of the biologically active material and an operator's exposure to the biologically active material. Because the biologically active material is applied after the formation of the coating layer, the temperature at which the coating layer can be processed is not limited by the temperature tolerance of the biologically active material.

5 DETAILED DESCRIPTION OF THE INVENTION

The method of the present invention includes providing a medical device having a surface adapted for exposure to body tissue of a patient. FIGS. 1-7 show a portion of a medical device 10 with a surface 20. Generally, the medical device can be inserted into and implanted in the body of a patient. For example, suitable medical devices include, but are not limited to, orthopedic, dental, cosmetic, cardiac, and vascular implants. More particularly, medical devices suitable for the present invention include, but are not limited to, stents, surgical staples, catheters, such as central venous catheters and arterial catheters, guidewires, cannulas, AV shunts, pacemakers, cardiac pacemaker leads or lead tips, cardiac defibrillator leads or lead tips, implantable vascular access ports, blood storage bags, blood tubing, vascular or other grafts, intraaortic balloon pumps, heart valves, cardiovascular sutures, total artificial hearts and ventricular assist pumps, and extracorporeal devices such as blood oxygenators, blood filters, hemodialysis units, hemoperfusion units and plasmapheresis units.

Medical devices of the present invention also include those that have a tubular or cylindrical-like portion. The tubular portion of the medical device need not be completely cylindrical. For instance, the cross-section of the tubular portion can be any shape, such as rectangle, a triangle, etc., not just a circle. Such devices include, without limitation, stents and grafts. A bifurcated stent is also included among the medical devices which can be fabricated by the method of the present invention.

Figure 3:
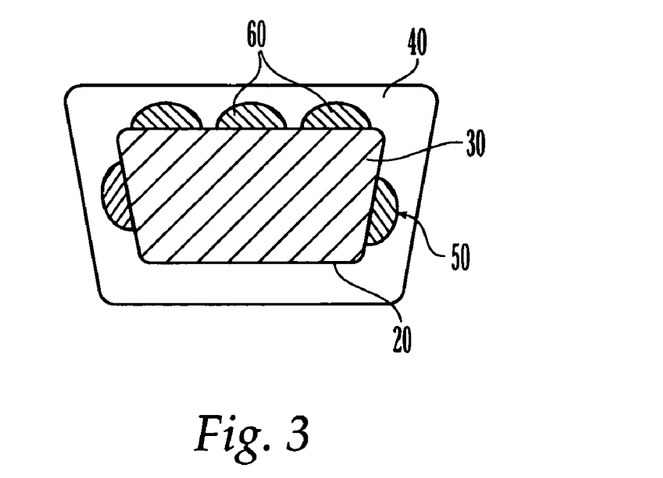
FIG. 3 is a cross-sectional view of an individual strut of a stent. The strut has a surface, a coating layer disposed thereon, and a plurality of pockets containing a biologically active material on the surface of the strut.

In addition, the tubular portion of the medical device may be a sidewall that is comprised of a plurality of struts. The struts may be arranged in any suitable configuration. Also, the struts do not all have to have the same shape or geometric configuration. Each individual strut 30 has a surface 20 adapted for exposure to the body tissue of the patient. The tubular sidewall may be a stent. When the medical device 10 is a stent comprising a plurality of struts 30, the surface 20 adapted for exposure to body tissue of a patient is located on a strut 30 as shown in FIG. 3. FIG. 3 shows a cross-sectional view of an individual strut 30 having a surface 20.

Medical devices which are particularly suitable for the present invention include any kind of stent for medical purposes which is known to the skilled artisan. Suitable stents include, for example, vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al. In preferred embodiments, the stent suitable for the present invention is an Express stent. In more preferred embodiments, the stent is Express™ stent and Express2™ stent (Boston Scientific Corp., Natick, Mass.).

The medical devices suitable for the present invention may be fabricated from metallic, polymeric, and/or ceramic materials. Metallic material is more preferable. Suitable metallic materials include metals and alloys based on titanium (such as nitinol, nickel titanium alloys, thermo-memory alloy materials), stainless steel, niobium, tantalum, nickel-chrome, or certain cobalt alloys including cobalt-chromium-nickel alloys such as Elgiloy® and Phynox®. Metallic materials also include clad composite filaments, such as those disclosed in WO 94/16646. Suitable polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins. Suitable ceramic materials include but are not limited to titaniumoxides, iridiumoxides, and hafniumoxides.

Figure 1:
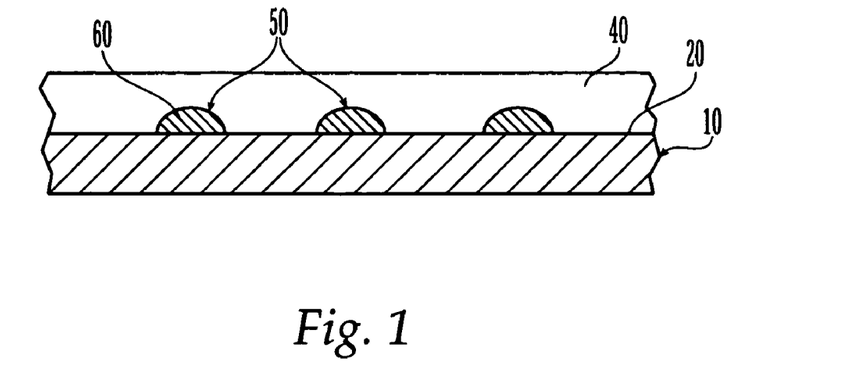
FIG. 1 is a cross-sectional view of a portion of a medical device of the present invention showing a medical device having a surface, a coating layer on the surface, and pockets containing a biologically active material on the surface of the medical device.
Figure 2:
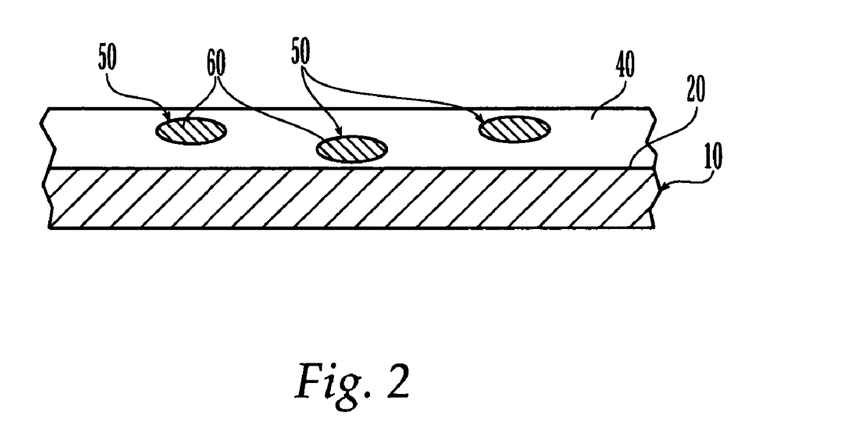
FIG. 2 is a cross-sectional view of a portion of a medical device of the present invention showing a medical device having a surface, a coating layer on the surface, and a plurality of pockets containing a biologically active material disposed in the coating layer at different depths.

A coating layer 40 is formed on at least a portion of the surface 20 of the medical device 10. FIGS. 1 and 2 are cross-sectional views of a portion of a medical device 10 having a surface 20, and a coating layer 40 disposed on the surface 20. The coating layer 40 may be continuous over the surface 20 of the medical device 10 or individual struts 30 to create a "wrap-around" effect so that the coating layer 40 is better adhered to the surface 20 of the medical device 10. FIG. 3 shows a cross-sectional view of a strut 30 having a continuous coating layer 40 on its surface 20. On the other hand the coating layer 40 can be formed only on a portion of the surface 20.

The coating layer 40 is preferably formed by disposing a coating formulation on at least a portion of the surface 20. The coating formulation preferably includes a polymer suitable for a medical device 10.

The polymer in the coating layer 40 should be a material that is biocompatible and avoids irritation to body tissue. The polymer may be a biostable polymer. Preferably, the polymers used in the coating composition of the present invention are selected from the following: styrene-isobutylene-styrene copolymers, polyurethanes, silicones (e.g., polysiloxanes and substituted polysiloxanes), and polyesters. Other polymers which can be used include ones that can be dissolved and cured or polymerized on the medical device. Still other polymers that may be used include ultraviolet cross-linkable polymers and/or high temperature setting thermoset polymers. Additional suitable polymers include thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (ethylene-propylene-diene monomer) rubbers, fluorosilicones, polyethylene glycol, polysaccharides, phospholipids, and combinations of the foregoing. Hydrogel polymers such as polyhema, polyethylene glycol, polyacrylamide, and other acrylic hydrogels may also be used. Other hydrogel polymers that may be used are disclosed in U.S. Pat. Nos. 5,304,121, 5,464,650, 6,368,356, PCT publication WO 95/03083 and U.S. Pat. No. 5,120,322, which are incorporated by references.

Medical devices may be coated or made with non-polymeric materials. Examples of non-polymeric materials include sterols such as cholesterol, stigmasterol, β-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; sphingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glycerol tristearate, stearic acid, stearic anhydride, glyceryl monooleate, glyceryl monolinoleate, and acetylated monoglycerides.

More preferably for medical devices 10 which undergo mechanical challenges, e.g., expansion and contraction, the materials for making or coating the medical device should be selected from elastomeric polymers such as SIBS, silicones (e.g., polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating composition is capable of undergoing deformation under the yield point when the device is subjected to forces, stress or mechanical challenge. The coating layer 40 may be a covering material for a medical device 10 such as a stent or a graft. As an alternative to using only polymers that are elastic, less elastic polymers (such as thermoset polymers) may be applied to portions of the device that are subjected to stress.

Preferably, the polymer is dispersed or dissolved in a solvent suitable for the medical device 10, which are known to the skilled artisan. The solvents used to prepare the coating compositions include ones which can dissolve the polymer into solution or suspend the polymer. Examples of suitable solvents include, but are not limited to, tetrahydrofuran, methylethylketone, chloroform, toluene, acetone, isooctane, 1,1,1,-trichloroethane, dichloromethane, and mixture thereof.

The coating formulation can be applied by any method to a surface 20 of a medical device 10 to form a coating layer 40. Examples of suitable methods include, but are not limited to, spraying such as by conventional nozzle or ultrasonic nozzle, dipping, rolling, electrostatic deposition, and a batch process such as air suspension, inject molding, pancoating or ultrasonic mist spraying. More than one coating method can be used to form a coating layer 40. The coating formulation is then dried to form the coating layer 40 using any suitable method. Preferably, the coating layer 40 itself is substantially free of biologically active materials. If the coating formulation does not contain a biologically active material, the coating formulation may be dried at a high temperature to form the coating layer 40, and the medical device 10 need not be weighed before and after forming the coating layer 40.

Preferably, the coating layer 40 is an elastic material or low durometer plastic such as ethylene vinyl acetate, low density polyethylene, so that the coating layer 40 may encapsulate the biologically active material that has been injected at the surface 20 of the medical device 10 and beneath the coating layer 40. The coating layer 40 is preferably soft enough to allow a needle to penetrate the coating layer 40 to inject a composition comprising a biologically active material.

The thickness of the coating layer 40 can range from a single layer of molecules to about 0.1 mm. Suitable thicknesses for the coating layer 40 are known in the art and can be selected by the skilled artisans.

Also, the coating layer 40 may be in any suitable form such as, but not limited to, a polymer matrix or a porous structure. Pores or channels may be formed in the coating layer 40 prior to injection of the biologically active material into the coating layer 40 by any suitable method. Dissolved gases such as $CO_2$ may be used followed by a pressure change to form pores or channels in the coating layer 40. A freeze-drying technique may also be used to form pores or channels in the coating layer 40. The freeze-drying technique involves applying a solvent to the coating layer 40, freezing the applied solvent and coating layer 40 (for example, with nitrogen), and applying a vacuum to the frozen combination. The lyophilized solvent may then be removed from the coating layer 40, leaving behind pores in the process. Microfibers may be included in the coating layer 40 and then removed to form channels in the coating layer 40. The microfibers may be removed by dissolving the coating layer 40 with a solvent, or the microfibers may be physically removed by pulling the microfibers out of the coating layer 40. Channels may also be formed in the coating layer 40 by tracking a small wire through the lumen of a needle injected into the coating layer 40 and under the coating layer 40 along the surface 20 of the medical device 10 or surface 20 of the struts 30 of a stent. These forms of the coating layer 40 may enhance the dispersion of the biologically active material after the biologically active material is disposed in the coating layer 40.

Figure 4:
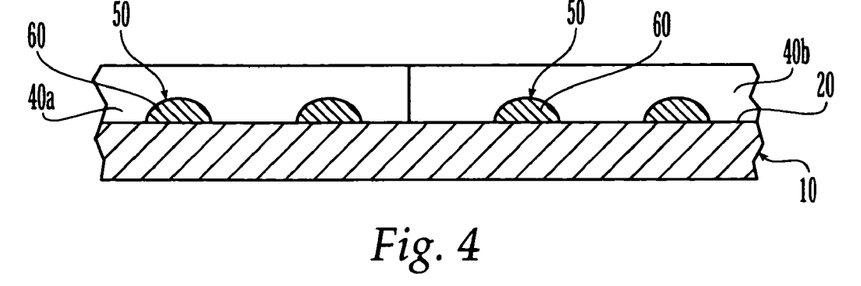
FIG. 4 is a cross-sectional view of a portion of a medical device of the present invention showing a medical device having a surface, two adjacent coating layers on the surface, and a plurality of pockets containing a biologically active material disposed in both coating layers.
Figure 5:
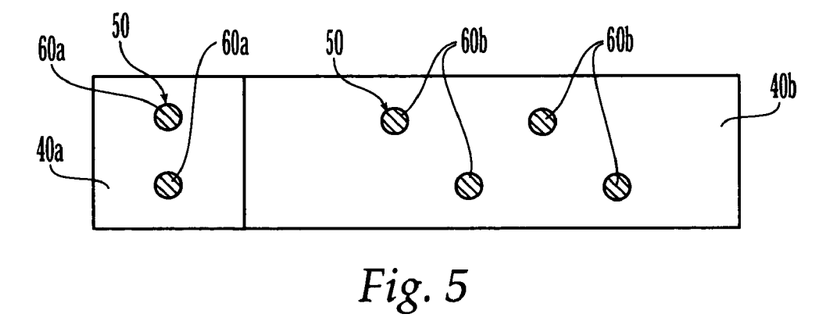
FIG. 5 is a plan view of a cross-sectional view of two coating layers, each having a plurality of pockets containing a biologically active material dispersed therein. The biologically active material in each coating layer is different.

Multiple coating layers 40 may be formed on the surface 20 of the medical device 10. The coating layers 40 may contain different materials, such as different polymers, or each coating layer 40 may contain the same combination of polymers, but contain different amounts of each polymer. For example, a first coating layer 40a and a second or additional coating layer 40b may contain different materials that release certain biologically active materials at different rates. Also, the coating layers 40a, 40b may be of different thicknesses and be arranged in any configuration on the medical device, such as disposed on different areas of the medical device 10 or the first coating layer 40a may cover the surface 20 of the medical device 10 and the second coating layer 40b may be disposed on the first coating layer 40a. For example, the coating layers 40a, 40b may be adjacent on the surface 20 of the medical device 10, as shown in FIGS. 4 and 5. FIG. 4 shows an embodiment with two coating layers 40a, 40b on different portions of the surface 20 of a medical device 10. FIG. 5 shows a plan view of a portion of a medical device 10 with two different coating layers 40a, 40b on the surface 20 of the medical device 10.

Figure 6:
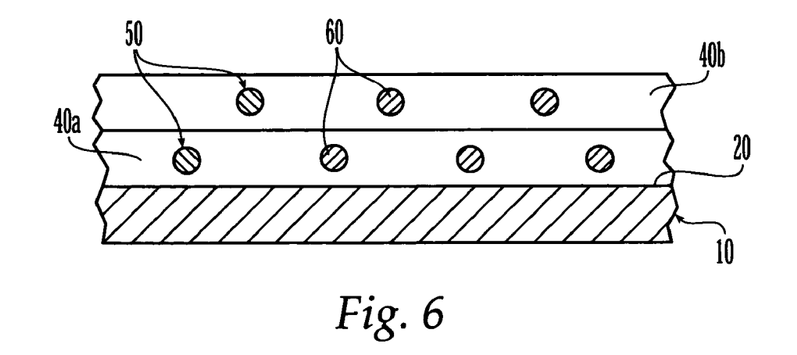
FIG. 6 is a cross-sectional view of a portion of a medical device of the present invention showing a medical device having a surface, a first coating layer disposed on the surface, a second coating layer disposed on the first coating layer, and a plurality of pockets containing a biologically active material disposed within both coating layers.

Alternatively, a first coating layer 40a may be disposed on the surface 20 of the medical device 10 and a second or additional coating layer 40b may be disposed over at least a portion of the first coating layer 40a. The second coating layer 40b may or may not also be disposed on the surface 20 of the medical device 10. FIG. 6 shows an embodiment having a first coating layer 40a disposed on the surface 20 of a medical device 10 and a second or additional coating layer 40b disposed on the first coating layer 40a.

The coating layers 40a, 40b may be formed using any suitable method, including the methods described above for depositing a coating composition to form a coating layer 40. For example, a first coating layer 40a may be applied over the entire surface 20 of the medical device 10 by a spraying process. Then, a portion of the first coating layer 40a may be ablated by a laser and a second coating layer 40b may be applied over the ablated portion using a spray process while masking the remaining portion of the first coating layer 40a.

A biologically active material 60 is dispersed within the coating layer 40. The term "biologically active material" encompasses therapeutic agents, such as drugs, and also genetic materials and biological materials. The genetic materials mean DNA or RNA, including, without limitation, of DNA/RNA encoding a useful protein stated below, intended to be inserted into a human body including viral vectors and non-viral vectors as well as anti-sense nucleic acid molecules such as DNA, RNA and RNAi. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Non-viral vectors include artificial chromosomes and minichromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endothelial Mitogenic Growth Factors, and epidermal growth factors, transforming growth factor and platelet derived endothelial growth factor, platelet derived growth factor, tumor necrosis factor, hepatocyte growth factor and insulin like growth factor), transcription factors, proteinkinases, CD inhibitors, thymidine kinase, monoclonal antibodies, and bone morphogenic proteins (BMP's), such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progentitor cells) stem cells (e.g., mesenchymal, hematopoietic, neuronal), pluripotent stem cells, fibroblasts, macrophage, and satellite cells.

Biologically active material 60 also includes non-genetic therapeutic agents, such as:
anti-thrombogenic agents such as heparin, heparin derivatives, urokinase, and PPack (dextrophenylalanine proline arginine chloromethylketone);
anti-proliferative agents such as enoxaprin, angiopeptin, geldanamycin or monoclonal antibodies capable of blocking smooth muscle cell proliferation, hirudin, acetylsalicylic acid, tacrolimus, everolimus, amlodipine and doxazosin;
anti-inflammatory agents such as glucocorticoids, betamethasone, dexamethasone, prednisolone, corticosterone, budesonide, estrogen, sulfasalazine, rosiglitazone, mycophenolic acid and mesalamine;
antineoplastic/antiproliferative/anti-miotic agents such as paclitaxel, 5-fluorouracil, cisplatin, vinblastine, vincristine, epothilones, epothilones D, methotrexate, azathioprine, adriamycin and mutamycin; endostatin, angiostatin and thymidine kinase inhibitors, cladribine, taxol and its analogs or derivatives;
anesthetic agents such as lidocaine, bupivacaine, and ropivacaine;
anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides;

DNA demethylating drugs such as 5-azacytidine, which is also categorized as a RNA or DNA metabolite that inhibit cell growth and induce apoptosis in certain cancer cells;

vascular cell growth promotors such as growth factors, Vascular Endothelial Growth Factors (FEGF, all types including VEGF-2), growth factor receptors, transcriptional activators, and translational promotors;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin and tobranycin;

antagonist for collagen synthesis, such as halofuginone;

angiogenic substances, such as acidic and basic fibroblast growth factors, estrogen including estradiol (E2), estriol (E3) and 17-Beta Estradiol;

drugs for heart failure, such as digoxin, beta-blockers, angiotensin-converting enzyme (ACE) inhibitors including captopril and enalopril, statins and related compounds;

fat-soluble vitamins A, D, E, K and their derivatives;

cortisone and its derivatives;

antiplatlet aggregation substance, phosphodiesterase inhibitor, such as cilostazole; and rapamycin (sirolimus), everolimus and tacrolimus.

Preferred biologically active materials include anti-proliferative drugs such as steroids, vitamins, and restenosis-inhibiting agents. Preferred restenosis-inhibiting agents include microtubule stabilizing agents such as Taxol, paclitaxel, paclitaxel analogues, derivatives, and mixtures thereof. For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other preferred biologically active materials include nitroglycerin, nitrous oxides, nitric oxides, antibiotics, aspirins, digitalis, estrogen derivatives such as estradiol and glycosides.

The biologically active material 60 is deposited underneath, on top of, or within the coating layer 40 after the coating composition has been applied to the surface 20 of the medical device 10 and dried to form the coating layer 40. The coating layer 40 encapsulates and holds the biologically active material 60 on the surface 20 of the medical device 10 or within the coating layer 40.

The biologically active material 60 is deposited within the coating layer 40 by injecting a composition comprising a biologically active material 60 into the coating layer 40 at one or more locations to form at least one pocket 50 containing the biologically active material 60. The term "pocket" refers to an indentation, receptacle, cavity, pore, or groove of any cross-sectional configuration, depth, shape, or size. Preferably, the pockets 50 have average diameters in the millimeter, micrometer, or nanometer, i.e., they are millipores, micropores, or nanopores. Preferably the average surface area of the pockets range from about 5% to about 90% of the outer surface area of the device. More preferably the average surface area of the pockets range from about 20% to about 50% of the outer surface area of the device. Preferably, the average volume of the pockets range from about 10 nanoliters to 10 picoliters, 10 picoliters to about 1000 picoliters, 10 picoliter to about 10 femtoliter range. FIG. 1 shows a plurality of pockets 50 containing a biologically active material 60 disposed on the surface 20 of a medical device 10, which is underneath the coating layer 40.

The pockets 50 can be situated in a regular pattern, such as in a row, or in an irregular pattern, and the pockets 50 may be spaced apart any desired distance, or may be interconnected. The pockets 50 may be uniformly or non-uniformly distributed in any pattern in the coating layer 40. For example, the pockets 50 may be more densely disposed in certain areas where a sustained release of the biologically active material 60 is desired. Thus, the biologically active material 60 may be localized in one or more areas within the coating layer 40 while other areas are substantially free of the biologically active material 60. The pockets 50 containing the biologically active material 60 may be accurately positioned in any configuration within the coating layer 40. For example, the pockets 50 may be configured so that there will be a sustained release of the biologically active material 60 from the coating layer 40 when the medical device is exposed to a body lumen. By adjusting the amount of biologically active material 60, the size and configuration of the pockets 50, and the thickness and composition of the coating layer 40, a desired distribution and release profile of the biologically active material 60 may be achieved.

There are several primary mechanisms by which active agents may be released from a delivery system: diffusion, convection, degradation, and swelling followed by diffusion or convection. Any or all of the mechanisms may occur in a given release system. Diffusion occurs when a drug or other active agent passes through the polymer that forms the controlled-release device. The diffusion can occur on a macroscopic scale—as through pores in the polymer matrix—or on a molecular level, by passing between polymer chains. Diffusion occurs when the drug passes from the polymer matrix into the external environment. As the release continues, its rate normally decreases with this type of system, since the active agent has a progressively longer distance to travel and therefore requires a longer diffusion time to release. Diffusion also depends on the type of polymers and the type of drugs. One of ordinary skill in the art would understand how to adjust these factors to obtain a desirable release profile. For example, a desired diffusion level may be achieved at least in part by customizing the thickness of the coating layer 40. Another alternative may be the introduction of a drug and a hydrophilic substance into the coating layer 40. When the hydrophilic substance subsequently swells, the biologically active material may be driven out of the coating layer 40. The use of hydrogel and/or osmotic agent that swells when in contact with liquid enhance the release of the agent through the pores that are formed in the polymer, including pores formed by injection needles. The release of drug can be controlled by the size of the pores created by the injection needles. Generally, a thin coating layer 40 will result in a faster release. Also, generally more voluminous pockets 50 with result in a longer release.

In addition, multiple coating layers 40 may be formed to adjust the release profile. When multiple coating layers 40 are formed on the surface 20 of the medical device, pockets 50 containing the same or different biologically active materials 60 may be deposited into each coating layer 40. The combination of coating layers 40 and biologically active materials 60 may be chosen to obtain desired release rates of the biologically active materials 60 from the coating layers 40. For example, a first coating layer 40*a* may include a first biologically active material 60*a* that is released in a short time period and a second coating layer 40*b* may include a second biologically active material 60*b* that is released over an extended period of time. FIG. 4 is a cross-sectional view of two coating layers 40*a*, 40*b*, each having a plurality of pockets 50 containing a biologically active material 60*a*, 60*b* dispersed therein. The biologically active material 60*a*, 60*b* in each coating layer 40*a*, 40*b* is different. FIG. 6 is a cross-sectional view of a portion of a medical device of the present invention showing a medical device having a surface 20, a first coating layer 40*a* disposed on the surface 20, a second coating layer 40*b* disposed on the first coating layer 40*a*, and a plurality of pockets 50 containing a biologically active material 60 disposed within both coating layers 40*a*, 40*b*.

Figure 7:
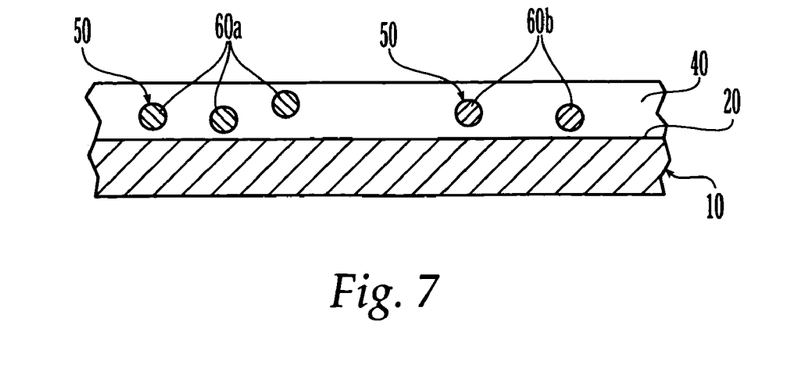
FIG. 7 is a cross-sectional view of a portion of a medical device of the present invention showing a medical device having a surface, a coating layer on the surface, and a plurality of pockets containing a biologically active material disposed in the coating layers. The pockets contain different biologically active materials.

The pockets 50 may contain different biologically active materials 60 or different combinations of biologically active materials 60. FIG. 7 is a cross-sectional view of a portion of a medical device 10 of the present invention showing a medical device 10 having a surface 20, a coating layer 40 on the surface 20, and a plurality of pockets 50 containing a biologically active material 60*a*, 60*b* disposed in the coating layers 40*a*, 40*b*. The pockets 50 contain different biologically active materials 60*a*, 60*b*.

The pockets 50 containing the biologically active material 60 can be formed in the coating layer 40 by any suitable method such as, but not limited to, needle injection, chemical etching, photo-etching, high-velocity particle impact ("blast methods"), needle-less injection ($CO_2$-powered or spring-loaded), stamping or laser ablation. Again, microfibers may be included in the coating layer 40 and then removed to form channels in the coating layer 40. The microfibers may be removed by dissolving the coating layer 40 with a solvent, or the microfibers may be physically removed by pulling the microfibers out of the coating layer 40. Pockets can also be formed by embedding magnetic micro-particles in a "soft" polymer and subsequently removing the micro-particles by magnetic attraction, thereby leaving open channels to the surface where the particles passed through.

Preferably, the plurality of pockets 50 containing the biologically active material 60 are formed by injecting the composition comprising a biologically active material 60 into or under the coating layer 40. The composition is injected into or under the coating layer 40 at one or more locations in the coating layer 40. If the drug composition is injected more than once at the same location, the drug composition should be substantially dried before more material is injected.

The composition may be deposited into the coating layer 40 in any suitable manner as known to one skilled in the art. The composition comprising the biologically active material 60 may be injected as a solid, such as in the powder form, or as a liquid. For example, if the composition only contains the biologically active material 60, it may be injected as a solid plug that is inserted into the coating layer 40 with a needle, cannula, or plunger. Preferably, the composition is injected as a liquid through a needle into the coating layer 40. Alternatively, at least one drug may be dissolved in water, then frozen into solid shape, and subsequently pushed into a "soft" polymer.

The needle should be small enough so that the opening in the coating layer 40 created by the needle leaves the coating layer 40 intact. Preferably, the needle is a nanometer-sized or micrometer-sized needle. Such needle injection devices are commercially available. For example, micro-injection needles are available from Harvard Apparatus of Holliston, Mass. Such needle injection devices allow for the precise measurement of the amount of biologically active material 60 injected and can also be automated and computer-controlled for efficient manufacture of the medical device 10. Dispensers that can inject as little as about 26 picoliters at a time are commercially available. For example, one suitable dispenser is the UltraMicroPump-II made by World Precision Instruments, Inc. of Sarasota, Fla. More than one needle can be used to inject the same or different biologically active material 60 at the same time or different times at different locations. In addition, using commercially available piezomotors in conjunction with image equipment, a precise location of the injection locations can be determined. The drug composition may be injected using a charge coupled device ("CCD") and robotics system. Specifically, a CCD camera with sufficient magnification will allow for precise positioning of an injection needle with respect to the stent. Precision piezomotors (e.g., Klocke system with a movement precision in the order of nanometers at strokes of millimeters) may then be used to feed the injection needle into the coating layer 40 using the CCD image as a feedback system to control the movement. Once the injection needle is at a desired location, which may be a predetermined location, the injection process may then be activated. The injection needle may also rotate in a spiral fashion along the longitudinal axis of the stent to reach desired injection sites.

The injection location can be calculated by measuring the thickness of the coating layer 40 and the position of the surface 20 of the medical device 10. One way to detect the position of the surface 20 of the medical device 10 is by monitoring the force needed to drive the needle forward. The position of the surface 20 can be monitored using sensors such as those used in atomic force microscopy. The thickness of the coating layer 40 at each injection location can be optically measured using a white light interferometer by adopting a wavelength that is partially transparent to the polymer. White light is defined as polychromatic light which contains lights of various wavelength. An interferometer is an optical instrument for measuring the thickness of a layer. The "Michelson interferometer" is a well-known example of an interferometer. A white light interferometer is commercially available, for example from Zygo Corporation. The white light interferometer may be connected to a computer wherein the data obtained by the white light interferometer is processed. Such systems are commercially available.

Any suitable amount of the composition may be injected into the coating layer 40. Preferably, the composition contains 1% to 100% of the biologically active material 60 and is injected in an amount from about 0.01 picoliter to 20 picoliters, about 20 picoliters to about 1000 picoliters. Such amounts may be injected one or more times into or under the coating layer 40 at one or more locations in the coating layer 40 until a desired amount of the biologically active material 60 is injected into the coating layer 40 in a desired distribution.

A solvent may be mixed with the biologically active material 60 to form a drug composition before being deposited in the coating layer 40 or a solvent may be injected before or after injection of the drug composition. Suitable solvents include, but are not limited to, tetrahydrofuran, methylethylketone, chloroform, toluene, acetone, isooctane, 1,1,1,- trichloroethane, dichloromethane, isopropanol, DMAC, isopropyl alcohol (IPA) water, and mixture thereof.

A solvent may slightly swell the coating layer 40 to enhance the deposition of the biologically active material 60 within the coating layer 40. The solvent may partially dissolve the coating layer 40 without affecting the integrity of the coating layer 40 since the amount of solvent used is very small. However, it may be preferable that the solvent does not swell the coating layer 40. In a specific embodiment, multiple solvents may be used to differentially control polymer swelling, drug diffusion in the polymer, and solubility of the drug during injection and diffusion into the swelled polymer. Different solvent mixes would provide different drug distributions in the coating resulting in coating layers having different release kinetics.

The solvent may be one, such as toluene, that dissolves the coating layer 40 but not the biologically active material 60. If the solvent swells the coating layer 40 but not the biologically active material 60, it will be easier for the biologically active material 60 to penetrate into the coating layer 40. The solvent may be one, such as water or isopropanol, that dissolves the biologically active material 60 but not the coating layer 40. Alternatively, the solvent may be one, such as THF or DMAC, that dissolves both, in which case the penetration depth of the biologically active material 60 may be extended as compared to the situation where only the coating layer 40 is swelled. For example, paclitaxel may be dissolved in a solvent such as acetyl-acetate or THF which will swell a coating layer 40. Also, many biologically active materials 60, such as heparin, will dissolve in a solvent such as saline and saline will swell a coating layer 40 comprising hydrogel. In addition, the solvent may dissolve neither or be a combination of such solvents. For example, microparticles of the biologically active material 60 may be suspended in a nonsoluble fluid such as water or above the saturation limit and then injected into the coating layer 40.

After a solvent has been injected into the coating layer 40, the solvent is preferably removed quickly, to restore the mechanical properties of the coating layer 40. The solvent may be removed by any suitable method, such as by evaporating, applying heat or pressure, applying a vacuum, removing the solvent with another solvent, or forming a gradient.

For example, a solvent, such as water, may be removed with isopropyl alcohol (IPA). Also, after injecting the solvent, a gradient in the concentration of the solvent throughout the coating layer 40 may be created to force the solvent to spread out and reach the outer surface 20 of the coating layer 40 where it will evaporate. This evaporation will sustain the gradient in concentration until all of the solvent has disappeared. In addition, a pressure gradient or chemical gradient may be created. The gradient may be created in any suitable manner.

The release profile of the biologically active material 60 can be adjusted by increasing the amount of the biologically active material 60 deposited in the coating layer 40 by using more solvent. The amount of the biologically active material 60 deposited could be enhanced by mixing the biologically active material 60 with a solvent which does not dissolve the coating layer 40, but merely swells it. Adjusting the amount of biologically active material deposited can affect the release rate of the biologically active material 60.

In addition to injecting a solvent before injecting the biologically active material 60, the release profile of the biologically active material 60 may be adjusted by having a concentration gradient of the biologically active material 60. For example, a wicking action to create surface tension will draw fluid and biologically active material 60 along the surface 20 of the medical device as the first coating layer 40 is dissolved by the solvent. The coating layer 40 allows diffusion of select biologically active materials 60 when applying an electrical gradient, chemical gradient, or pressure gradient from one end of a stent or other medical device to the other end. These gradients can be created using any suitable method, such as gel electrophoresis, ion exchange column chromatography, and HPLC.

When the coating layer 40 comprises an elastic material, the injection needle will merely push aside the coating layer 40 to form a channel and removing the needle will close the channel so that the biologically active material 60 will-be encapsulated within the coating layer 40. In addition, when a solvent is injected, the solvent will run up the channel when the needle is withdrawn from the coating layer 40, thereby dissolving the coating layer 40 around the channel. The swelled coating layer 40 will close the space formed by the needle. In addition, applying heat or pressure will force the dissolved channel to resolidify without leaving an opening in the coating layer 40. Also, the channel created by the needle may be left intact to facilitate release of the biologically active material 60. The channel may be sealed in any other suitable manner, such as by inserting a solid biologically active material 60 or polymer plug with a needle or cannula or disposing a coating composition over the biologically active material 60 to fill the channel. The coating composition disposed in the channel may be the same or different than the coating composition used to form the coating layer 40 as long as the coating composition applied over the biologically active material 60 bonds to the coating layer 40.

The following example shows calculations for determining the number and size of injections needed to deliver a certain amount of biologically active material 60 into a coating layer 40 disposed on the surface 20 of a 9 nm metal stent. In this example, the coating layer 40 comprises a biostable polymer, and the biologically active material 60 in the composition is paclitaxel.

The total weight of the polymer and paclitaxel to be coated on the stent is 0.250 mg. Assuming the paclitaxel is present in an amount of 25% of the total weight, then the total amount of paclitaxel would be 0.062 mg which equals about 62 nanoliters or about 62,000 picoliters of paclitaxel. If it is desirable to have 100 pockets of paclitaxel, then each pocket would contain a volume of 620 picoliters of paclitaxel. The paclitaxel is deposited into the coating layer by needle injection. The volume of each injection of paclitaxel is selected to be approximately 26 picoliters of paclitaxel. Thus, multiple injections would be required to deposit the desired 620 picoliters of paclitaxel at each location to form a pocket. In particular, if there are approximately 26 picoliters of paclitaxel per injection, then 24 injections would be required to deposit 620 picoliters of paclitaxel at each location to form a pocket. The paclitaxel may be injected in solid form. Alternatively, paclitaxel may be injected with a solvent, e.g., chloroform.

With a 9 mm stent having a plurality of struts, the width of each strut is approximately ⅙ of a mm or 0.167 mm. The polymer coating layer 40 has a thickness of about 10 to about 20 micrometer. The paclitaxel is injected using a needle with glass drawn to fit to a luer lock having an outer diameter of 0.005 mm, which is less then about 4% of the width of the strut. A solvent may be used to swell the coating layer 40 prior to injection. In such case, the hole left by the injection needle would be smaller due to the swelling of the coating layer 40. The hole may also be closed after injection by applying either heat or pressure.

To advance the needle all the way to the metal surface 20 of the stent, an ordinary microscope or an automatic system with a CCD camera and robotics may be used to position the needle over the stent (or vice versa). Such nanorobotics systems are commercially available from, for example, Klocke Nanotechnik of Aachen, Germany.

To determine the coating layer 40 thickness on every injection location on the stent, white light interferometry may be used. Once the needle is advanced to the specific strut were the paclitaxel is to be injected, the needle is advanced forward to the metal surface 20, a particular amount of the paclitaxel is injected, and the needle is withdrawn. If necessary, the hole left by the needle could be closed by using a second needle injecting a small amount of polymer and a solvent such as toluene into the hole.

As known to one skilled in the art, similar calculations may be used for making other medical devices 10 with other biologically active materials 60 and coating layer 40 materials.

In use, a coated medical device 10, such as an expandable stent, according to the present invention can be made to provide a desired release profile of the biologically active material 60. Also, the medical devices 10 of the present invention may be used for any appropriate medical procedure. Delivery of the medical device 10 to a body lumen of a patient can be accomplished using methods well known to those skilled in the art, such as mounting a stent on an inflatable balloon disposed at the distal end of a delivery catheter. The biologically active material 60 diffused through the coating layer 40 to the body lumen.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

We claim:

1. A method of making a medical device having a surface, wherein at least a portion of the surface is covered with a coating layer comprising at least one pocket containing a biologically active material, the method comprising:
   (a) disposing a coating formulation comprising a polymer on at least a portion of the surface to form the coating layer; and
   (b) forming at least one pocket in the coating layer by injecting a composition comprising a biologically active material into or under the coating layer at one or more locations.

2. The method of claim 1, wherein the coating layer formed in step (a) is substantially free of any biologically active material.

3. The method of claim 1, wherein the polymer is a biostable polymer.

4. The method of claim 1, wherein the polymer is a hydrogel polymer.

5. The method of claim 1, wherein the coating layer formed in step (a) is in the form of a polymeric matrix.

6. The method of claim 1, wherein the composition is injected into the coating layer using a micrometer- or nanometer-sized needle.

7. The method of claim 1, wherein the composition is substantially free of any polymer.

8. The method of claim 1, wherein the composition comprises a hydrogel polymer.

9. The method of claim 1, wherein the biologically active material is selected from the group consisting of paclitaxel, paclitaxel analogues, paclitaxel derivatives, and combinations thereof.

10. The method of claim 1, wherein the biologically active material is a genetic material.

11. The method of claim 1, wherein the composition further comprises a radioactive material.

12. The method of claim 1, wherein the composition is injected in an amount of about 20 picoliters to about 0.1 microliter per injection.

13. The method of claim 10, wherein the composition is injected in an amount of about 10 nanoliters to about 20 picoliters per injection.

14. The method of claim 1, wherein at least one pocket containing the biologically active material contacts the surface of the medical device.

15. The method of claim 1, wherein the pocket containing the biologically active material has an average volume of about 20 picoliters to about 0.1 microliter.

16. The method of claim 1, wherein a plurality of pockets containing the biologically active material are formed and the pockets are interconnected.

17. The method of claim 1, wherein a plurality of pockets containing the biologically active material are formed and are non-uniformly dispersed in the coating layer.

18. The method of claim 1, wherein a plurality of pockets containing the biologically active material are formed and the pockets have different sizes.

19. The method of claim 1, wherein more than one composition comprising a biologically active material is injected into the coating layer.

20. The method of claim 19, wherein the compositions comprise different biologically active materials.

21. The method of claim 19, wherein the compositions contain different concentrations of the same biologically active material.

22. A method of making a coated stent having a surface, wherein at least a portion of the surface is covered with a coating layer, the method comprising:
   (a) providing a stent having a surface;
   (b) disposing a coating formulation comprising a polymer on at least a portion of the stent surface to form a coating layer, wherein the coating layer is substantially free of any biologically active material; and
   (c) injecting a composition comprising a biologically active material into or under the coating layer using a micrometer- or nanometer-sized needle,
   wherein the composition is injected into or under the coating layer at a plurality of locations to form a plurality of pockets containing the biologically active material.

23. The method of claim 22, wherein the composition is substantially free of a polymer.

24. The method of claim 22, wherein the composition comprises a hydrogel polymer.

25. The method of claim 22, wherein the biologically active material is selected from the group consisting of paclitaxel, paclitaxel analogues, paclitaxel derivatives, and combinations thereof.

26. A method of making a medical device having a surface, wherein at least a portion of the surface is covered with a coating layer comprising a plurality of pockets containing a first biologically active material, the method comprising:
   (a) disposing a first coating formulation comprising a first polymer on at least a portion of the surface to form a first coating layer, wherein the first coating layer is substantially free of any biologically active material; and (b) forming a plurality of pockets in the coating layer by injecting a first composition comprising a first biologically active material into or under the first coating layer at a plurality of locations, wherein the first composition is substantially free of a polymer.

27. The method of claim 26, wherein the polymer is a biostable polymer.

28. The method of claim 26, wherein the polymer is a hydrogel polymer.

29. The method of claim 26, further comprising forming an additional layer, wherein the additional coating layer is formed by disposing a second coating formulation that comprises a second polymer over the first coating layer.

30. The method of claim 29, wherein the additional coating layer is substantially free of any biologically active material.

31. The method of claim 29, wherein the first and second coating formulations comprise different polymers.

32. The method of claim 29, further comprising injecting a second composition comprising a second biologically active material into or under the second coating layer at a plurality of locations to form a plurality of pockets containing the second biologically active material.

33. The method of claim 29, wherein the first and second compositions comprise different biologically active materials.

34. The method of claim 29, wherein the compositions contain different concentrations of the same biologically active material.

35. The method of claim 29, wherein the first and second compositions are injected into the first and second coating layers using a micrometer- or nanometer-sized needle.

36. The method of claim 26, wherein the biologically active material is selected from the group consisting of paclitaxel, paclitaxel analogues, paclitaxel derivatives, and combinations thereof.

37. The method of claim 26, wherein the first composition is injected into or under the first coating layer so that at least one pocket containing the first biologically active material contacts the surface of the medical device.

38. The method of claim 26, wherein the pockets containing the first biologically active material have an average volume of about 20 picoliters to about 0.1 microliter.

39. The method of claim 26, further comprising injecting a solvent into a location in or under the first coating layer prior to injecting the composition into that location, and removing the solvent from that location.

40. The method of claim 39, wherein the solvent is removed by evaporation, applying heat or pressure, or creating a gradient.

* * * * *

UNITED STATES PATENT AND TRADEMARK OFFICE
CERTIFICATE OF CORRECTION

| | | |
|---|---|---|
| PATENT NO. | : 7,601,382 B2 | Page 1 of 1 |
| APPLICATION NO. | : 10/914012 | |
| DATED | : October 13, 2009 | |
| INVENTOR(S) | : Weber et al. | |

It is certified that error appears in the above-identified patent and that said Letters Patent is hereby corrected as shown below:

On the Title Page

Item [*] Notice:    Subject to any disclaimer, the term of this patent is extended or adjusted under 35 USC 154(b) by 779 days Delete the phrase "by 779 days" and insert -- by 1,182 days --

Signed and Sealed this

Sixth Day of April, 2010

David J. Kappos
*Director of the United States Patent and Trademark Office*